United States Patent [19]
Niskin et al.

[11] 4,347,751
[45] Sep. 7, 1982

[54] ELECTRIC WATER SAMPLING DEVICE

[76] Inventors: Shale J. Niskin, 3415 Chase Ave., Miami Beach, Fla. 33140; Gerald J. Williams, 485 Ridgewood Rd., Dade County, Fla.

[21] Appl. No.: 225,100

[22] Filed: Jan. 14, 1981

[51] Int. Cl.³ ............................................... G01N 1/12
[52] U.S. Cl. ................................................. 73/864.33
[58] Field of Search ........... 73/864.63, 864.64, 864.65, 73/864.66, 864.67

[56] References Cited

U.S. PATENT DOCUMENTS

| | | |
|---|---|---|
| 3,367,190 | 2/1968 | Bieri . |
| 3,489,012 | 1/1970 | Niskin . |
| 4,037,477 | 7/1977 | Niskin . |
| 4,091,676 | 5/1978 | Niskin . |

*Primary Examiner*—S. Clement Swisher
*Attorney, Agent, or Firm*—William A. Newton

[57] ABSTRACT

Disclosed is a water sampler device for collecting a sample of water at a desired depth, the water sampler device comprising a tubular member having at each end a rotatably mounted ball valve, a valve pulley mounted on the exterior of the tubular member and coupled to the ball valve for rotating the same, a center pulley mounted on the tubular member between the valve pulleys, an endless belt positioned around the three pulleys, an electric motor coupled to rotate the third pulley, electric circuitry for activating the electric motor and then deactivating the electric motor to open the ball valves at a desired level and then subsequently closing the ball valve at a level whereat the sample is taken.

14 Claims, 8 Drawing Figures

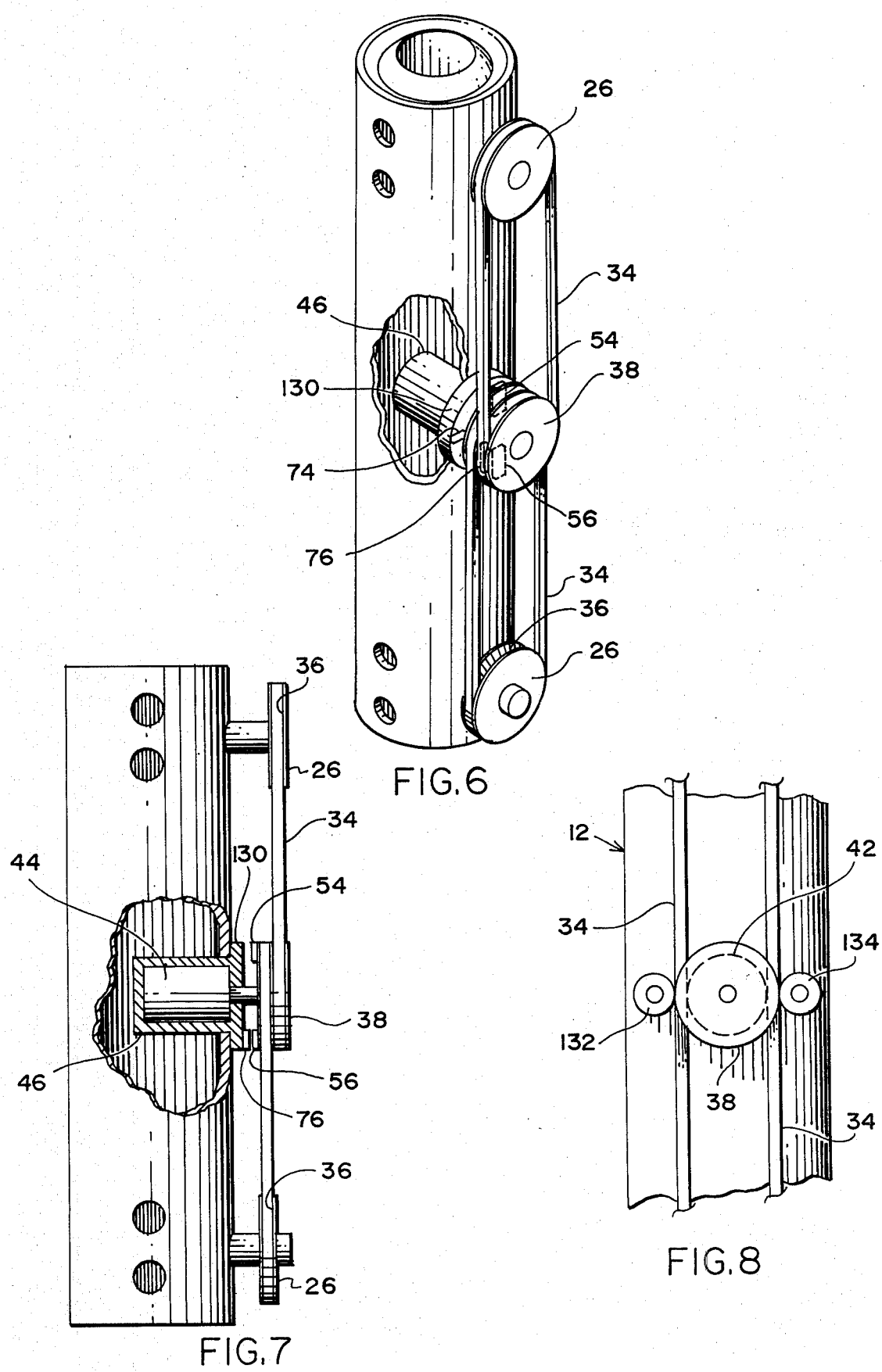

ELECTRIC WATER SAMPLING DEVICE

BACKGROUND OF THE INVENTION

1. Field of the Invention

This invention relates to water sample collecting devices and is more particularly directed to such a device having an open ended tubular member with a rotatable valve at each end for collecting and containing a sample of water taken from a predetermined depth in a body of water.

2. Description of the Prior Art

In location whereat a sample of water at a predetermined depth is desired, it is common to find the surface of the body of water to often be badly contaminated. In order to eliminate contamination problems, the water sampling devices of U.S. Pat. Nos. 4,037,477 and 4,091,676, to the applicant herein, were developed. More specifically, a water sampler device was developed to have a hollow, rigid, tubular member with ball valves at each end that are in a closed position at the time the device is launched and are maintained closed for a relatively short period until the sampler device has reached a desired depth. At the desired depth the ball valves are rotated to an open position to permit water to flush through the tubular member until the tubular member has reached the depth at which the sample is to be taken. At this depth, the ball valves are then closed, and the tubular member is raised to the surface.

To accomplish the above described position changing of the ball valves, an elaborate mechanical system was created. To set these prior art water samplers, lanyards must be manually grasped and pulled until the pulleys to which they are attached rotate against the force of power cords to reach a position where the ball valves are initially closed and will thereafter rotate in two increments of 90° when the lanyards are released.

In colder latitudes, the operation of grasping and forceably pulling the lanyards, and then locking the end of the lanyards into a latch proves to be very difficult, in that such operations must be conducted with gloves.

Accordingly, it can readily be seen that there is a need in the art for a water sampler device of the type described wherein the means for rotating the ball valves is mechanically simple and does not require manual dexterity.

U.S. Pat. Nos. 4,091,676; 4,037,477; and 3,489,012, all to Niskin, are incorporated herein by specific reference.

SUMMARY OF THE INVENTION

The invention is directed toward a water sampler device having at each end a rotatable ball valve for containing a sample of uncontaminated water collected at a desired depth in a body of water. The ball valves are rotated by pulleys mounted on the outside of the tubular member. The improvement of the present invention comprises having an electric motor drive an endless belt wrapped around the two pulleys. Means are provided for starting and stopping the electric motor when the tubular member is at a desired depth where its ball valves are to be opened. Likewise, means are provided for starting and stopping the electric motor to close the ball valves at a predetermined depth whereat the water sample is to be taken.

In the preferred embodiment, a third pulley is mounted between the two valve pulleys and engages the endless belt. The electric motor is coupled to the third pulley for rotation of the same. After the electric motor is activated to rotate the third pulley, the electric motor is deactivated by means disposed in position-sensing relationship to the third pulley. This allows for the ball valves to be rotated to their open position. When the ball valves are to be closed at the level whereat the sample is to be taken, the electric motor is again activated and, when the ball valves reach their closed position, means disposed in position-sensing relationship to the third pulley deactivate the electric motor.

BRIEF DESCRIPTION OF THE DRAWINGS

Further objects and advantages of the present invention will become apparent as the following description proceeds, taken in conjunction with the accompanying drawings in which:

FIG. 6 is a perspective view of another embodiment of the invention.

FIG. 7 is an elevational view of the embodiment of FIG. 6 with parts broken away.

FIG. 8 is an elevational view of the pulley arrangement of the embodiment of FIG. 6.

DESCRIPTION OF THE PREFERRED EMBODIMENTS

Figure 1:
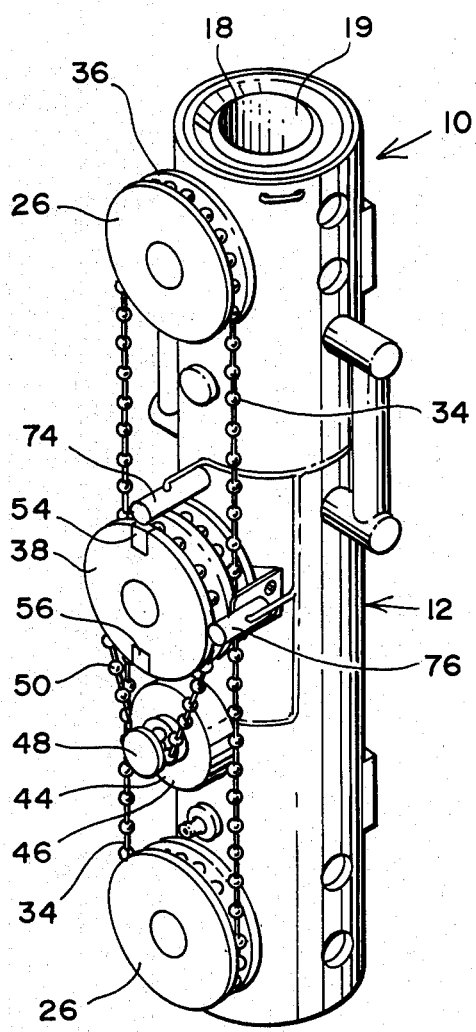
FIG. 1 is a perspective view of the tubular member of the water sampling device of the present invention.
Figure 2:
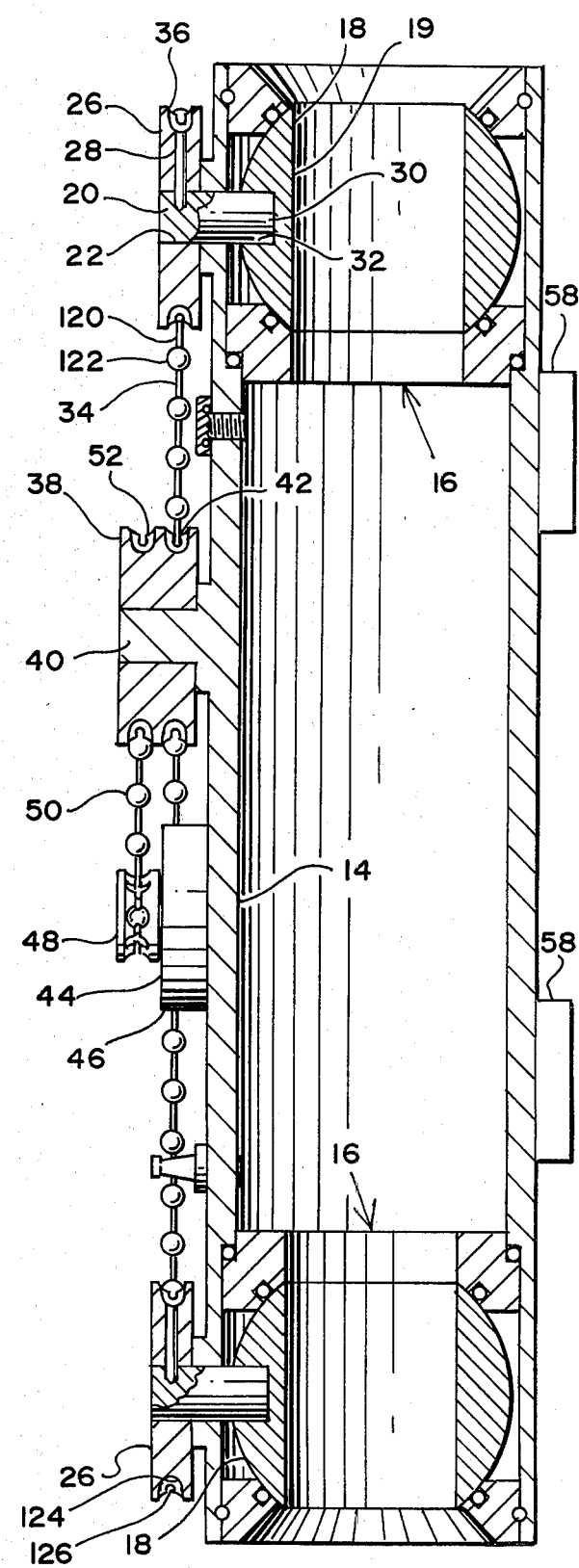
FIG. 2 is a cross-sectional view of the tubular member of FIG. 1 taken along section lines 2—2.

Referring to FIGS. 1 and 2, disclosed is a water sampling device 10 having an elongated tubular member or bottle 12 with a chamber 14, which is adapted to collect and retain a water sample therein. The specific construction of tubular member 12 is per se not part of the invention and suitable designs for the tubular member are shown in U.S. Pat. Nos. 4,037,477 and 4,091,676, which have been incorporated herein. For clarity and understanding, only the specific structure of the tubular member 12 that will assist in understanding the invention will be described.

As shown in the two above-referenced patents, at each end of the tubular member 12, there is provided a valve chamber 16 constructed and arranged to retain a spherical ball valve 18 therein. The specific design of the valve chambers 15 can take the form of those described in the two above-referenced patents, with the preferred design being found in U.S. Pat. No. 4,091,676. The ball valves 18 are the same in construction and operation and are each provided with an opening 19 that extends radially through the valve body for the flow of water into the tubular member 12 when in its open position, as shown in FIG. 2.

With reference to FIG. 2, the means for rotating the ball valves 18 differ slightly from the above-referenced patents in that the pulleys are rigidly attached directly to the valve stem. More specifically, a valve stem 20 is rotatably mounted in an opening 22 in a boss 24 formed in said tubular member 12. A valve pulley 26 is rigidly mounted to the outer end of the valve stem 20 by fastner means 28, which can be in the form of a nut and bolt. As with the designs of the above-referenced patents, the inner end of the valve stem 20 is provided with a rectangular shaped finger portion 30 that is fitted into a similarly shaped slot 32 formed on the ball valve 18.

As will be described in greater detail hereinafter, the ball valves 18 rotate 90 degrees from an initially closed position to an open position, then continue to rotate another 90 degrees to a further closed position, whereby the ball valves 18 and the valve pulleys 26 rotate through a complete arc of 180 degrees.

The improvement of the present invention is directed toward means for operating the pulleys 26 to provide the above-described operation. More specifically, an endless belt 34 is looped around the valve pulleys 26 so as to be secured in peripheral grooves 36 of the pulleys 26. A center or third pulley 38 is rotatably on an arm 40 secured to the tubular member 12. All three pulleys, the two 26's and 38, are aligned on the same axis and the pulley 38 has a diameter equal to or greater than that of the pulleys 26 so that a first peripheral groove 42 of the third pulley 38 tightly engages the endless belt 34. In the preferred embodiment, the third pulley 38 has the same diameter as the valve pulleys 26, so that the rotation of the pulley 38 through a 90° arc likewise rotates the valve pulleys 26, and therefore the ball valves 18, through a 90° arc.

An electric motor 44 is mounted on the exterior of the tubular member 12 in a waterproof housing 46 with a drive shaft 48 extending therefrom. A second endless belt 50 is wrapped around a second peripheral groove 52 of the third pulley 38. A pair of opposed magnets 54 and 56 are oppositely mounted on the peripheral circumference of the third pulley 38 along an axis passing through the center of rotation, i.e., 180° apart with respect to the center of the pulley 38.

Figure 3:
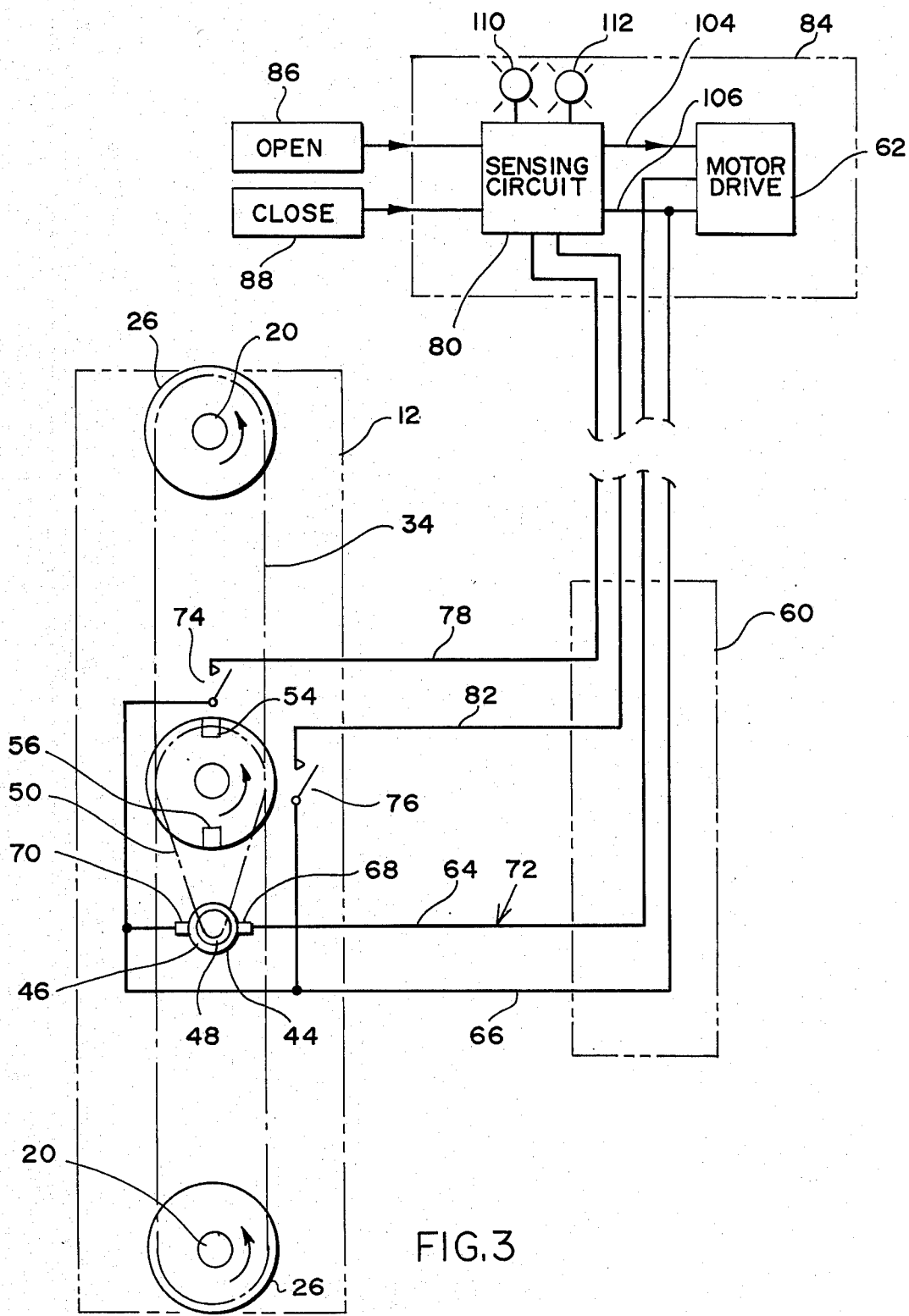
FIG. 3 is a schematic view of an electrical circuit for the water sampling device.

Preferably, but not necessarily, the tubular member 12 is mounted by a pair of wedge shaped brackets 58, secured to the side of the tubular member 12, to a rosette multi-bottle array system 60, such as that shown in U.S. Pat. No. 3,489,012, which has been incorporated herein. This rosette system 60 is schematically illustrated in FIG. 3. However, it should be understood that the tubular member 12 could also be suspended by itself on a single cable, such as illustrated in the U.S. Pat. Nos. 4,091,676 and 4,037,477.

Referring specifically to FIG. 3, a diagramic schematic illustrates the electrical system of the present invention. Electric power is provided from a motor drive and power source 62 over electrical conductors 64 and 66 to the terminals 68 and 70 of the electric motor 44, so as to define an energizing circuit 72. A pair of conventional magnetic activated switches 74 and 76 are positioned adjacent the periphery of the third pulley 38 and are at right angles to each other with respect to the center of the pulley 38. Each time one of the magnets 54 or 56 pass by one of the switches 74 or 76, the conductivity state of the switches are reversed from their preexisting state of being opened to their changed state of being closed. The first switch 74 is disposed in circuit interrupting relationship to a conductor 78, which is electrically coupled between a switch contact sensing circuit 80 and the conductor 66. The second switch 76 is disposed in circuit interrupting relationship to a conductor 82, which is electrically coupled between the switch contact sensing circuit 80 and the conductor 66. As shown in U.S. Pat. No. 3,489,012, the rosette system 60 is normally supported by a multi-conductor power cable. The conductors 78, 82, 64, and 66, in the preferred embodiment, are passed through the rosette system 60 and to, for example, a support ship through such a multi-conductor power cable. The power drive 62 and sensing circuit 80 are preferably situated on the ship in a control unit 84. Such a control unit ideally has a first or "open" control button 86 for activating the motor drive 62 to energize the electric motor 44 to move the ball valves 18 from their initially closed position to their open position. Subsequently, a second or "close" control button 88 activates the motor drive 62 to energize the electric motor 44 to move the ball valves 18 from their open position to a second or further closed position. It will be understood by those skilled in the art that a power cable with fewer conductors could be used, if desired, by using multiplexing circuitry at each end.

In operation, the water sampler device 10, mounted on the rosette system 60, is lowered, for instance from a ship, into the water whereon contaminates are floating on the surface of the water or just below the surface of the water. The tubular member 12 is normally filled with water before entering the body of water. The contaminated water cannot enter the tubular member 12 because the ball valves 18 are in their closed position. After lowering the tubular member 12 a relatively short distance into the water, as can be determined by the length of cable lowered, an operator manually presses the first button 86 on the control unit 84 to apply power through the energizing circuit 72 to the electric motor 44. The motor 44 continues to turn until one of the magnets 54 or 56 closes the normally open first switch 74. The sensing circuit 80 detects the closing of the first switch 74 and deactivates the electric motor 44 by removing power therefrom, thus latching the ball valves 18 in their open position, as shown in the Figures. The rosette system 60 is further lowered with the ball valves 18 in their open positions, permitting the water to flow through the entire length of the tubular member 12 to flush the same continuously during the lowering process. When the sampling device 10 has arrived at the predetermined depth whereat a sample of water is desired, as determined by the length of cable lowered, the operator wil push the second button 88 on the control unit 84. Again, power is applied through the energizing circuit 72 to the electric motor 44. Again, the motor 44 continues to turn until one of the magnets 54 or 56 closes the normally open second switch 76. The sensing circuit 80 detects the closing of the second switch 76 and deactivates the motor 44 by removing power therefrom, thus latching the ball valves in their closed positions. The tubular member 12 is then raised to the surface of the water, without contaminates entering therein.

In the above sequence, the pulleys 26 and 38 and the ball valves 18 are rotated initially through an arc of 90 degrees to move the ball valves 18 from their initially closed position to their open position. Thereafter, the ball valves 18 are rotated again by 90° to move the ball valves from their open position to again being in a closed position. The rotation of both moves is in the same direction. It will be obvious to those skilled in the art that the power to the motor 44 could be reversed in polarity so as to reverse the direction of rotation, leading to the ball valves 18 retracting their original rotation. This accomplishes the same results of ending up in a closed position.

Although the preferred embodiment has been shown with magnetically activated switches 74 and 76, it will be obvious to those skilled in the art that such switches can be replaced by cam operated micro-switches. Additionally, water pressure sensitive devices can be included in the rosette system 60 or the tubular member 12 for automatically initiating the motor 44, instead of manually operating the control buttons 86 and 88.

Figure 4:
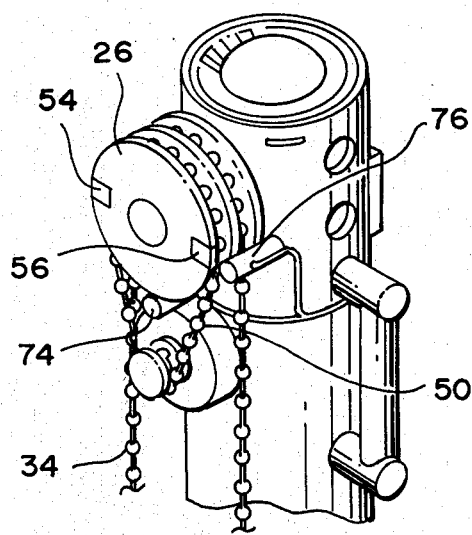
FIG. 4 is a fragmentary perspective view of a modification of the invention.

Although less desirable, the electric motor 44 could be directly coupled by the endless belt 50 to one of the pulleys 26. In this case, the center pulley 38 would be eliminated, and the magnets 54 and 56 would be positioned on one of the pulleys 26, with the switches 74 and 76 being positioned adjacent the pulley 26, as illustrated in FIG. 4.

Figure 5:
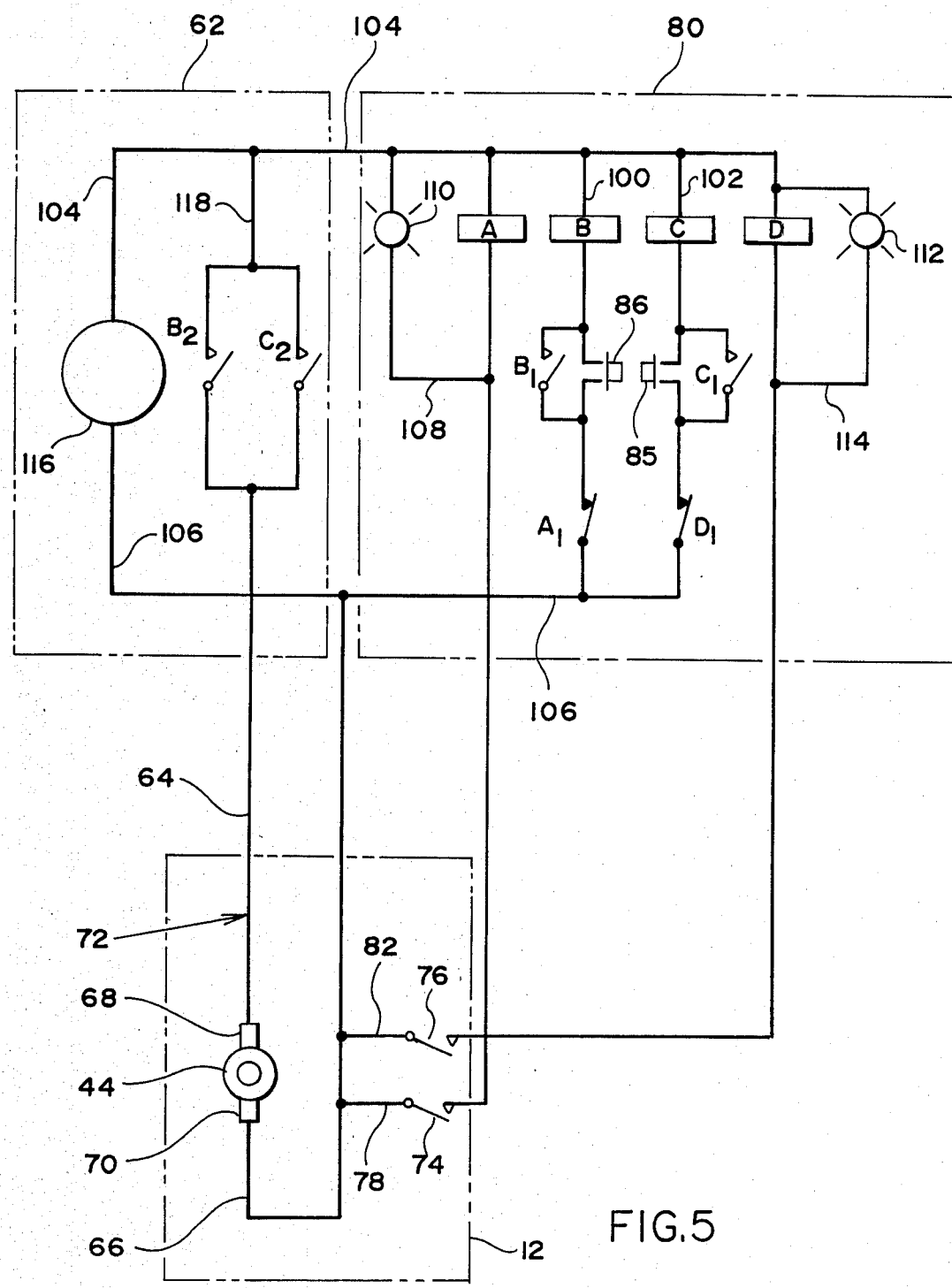
FIG. 5 is a more detailed schematic view of the electrical circuitry of FIG. 3.

FIG. 5 illustrates a more detailed electrical schematic of the circuitry of the present invention. More specifically, the components of the motor drive and power source 62 and the switch contact sensing circuit 80 are specifically illustrated. The sensing circuit 80 comprises four relays A, B, C, and D electrically coupled in parallel with respect to each other by the electrical conductors 78, 100, 102, and 82. These four lines are electrically coupled at one end to a first power conductor 104 and at their other end directly to a second power conductor 106 or indirectly to the second power conductor 106 through the conductor 66. The relay A has a first relay contact A1 positioned to electrically interrupt the circuit of conductor 100. The relay B has a relay contact B1 that shunts the button 86, which is in circuit interrupting relationship to the conductor 100. The relay C has a relay contact C1 which shunts the button 88, the button 88 being in circuit interrupting relationship to the circuit of the conductor 102. A conductor 108 is coupled from the conductor 78 to the power conductor 104 through a first light indicator 110. A second light indicator 112, through the conductor 114, shunts the relay D.

The motor drive and power means 62 comprises a power source 116 connected at one terminal to the power conductor 104 and at the other terminal to the power conductor 106. The conductor 64 is connected to a parallel combination of a relay contact B2 of the relay B and a relay contact C2 of the relay C. This parallel combination is connected by a conductor 118 to the power conductor 104. All of the relay contacts in the drawing are shown in their un-operated positions.

In operation, the operator pushes the "open" button 86, completes the circuit of conductor 100 so that the relay B is energized. The relay B operates to close the relay contact B1 and the relay contact B2. The relay contact B1, upon closing, latches the relay B in its energized, operated state. The closing of the relay contact B2 causes power to be applied from the power source 116 to the electric motor 44. As previously described, the electric motor 44 turns the pulley 38 until one of the magnets 54 or 56 closes the switch 74, which is a reed switch. The closing of switch 74 actuates the relay A and the light indicator 110. The energized relay A opens the relay contact A1, which in turn releases the relay B; thus removing power from the electrical motor 44. Hence, the indicator lamp 110 indicates that the ball valves 18 are in their open position.

A similar sequence of events occurs, involving the relays C and D, when the "closed" button 88 is pushed. Briefly, the pushing of the button 88 completes the circuit of the conductor 102 to energize the relay C, which closes the relay contact C1 and C2. The closed contact C1 latches the relay C in its operated state. The closed contact C2 applies power to the motor 44. The motor turns until the reed second switch 76 closes. The closing of the switch 76 actuates the relay D and the light indicator 112, with the relay D subsequently opening the relay contact D1. The opening of the relay contact D1 releases the relay C, thus removing power from the motor 44.

In practice, it will be obvious to those skilled in the art, that the above structure can be made from solid state components and integrated circuits with the principle operation remaining essentially the same.

In the embodiments shown in FIGS. 1, 2, and 4, the endless belt 34 preferably but not necessarily, takes the form of a chain and ball arrangement wherein the chain 120 has a plurality of balls 122. The grooves, such as grooves 36, 42 and 52, are configured to define alternating pockets 124 and reduced diameter channels 126, with the reduced diameter channels 126 receiving the exposed chain 120 and the pockets 124 receiving the balls 122. In this manner, the pulleys 26 and 38 securely engage the belts 34 and 50 so as to prevent slippage. However, there are other means in which these objectives can be accomplished, as will be shown in the hereinafter described embodiment.

FIGS. 6 through 8 disclose an alternative embodiment of the water sampling device 10, which has proven to be the preferred and most desirable design. The housing 46, with the electric motor 44 positioned therein, is mounted in the wall of the tubular member 12 so that a substantial portion of the housing 46 extends into the interior of the tubular member 12. The housing 46 and the electric motor 44 are directly positioned and aligned underneath the third pulley 38 so that the drive shaft 48 can be directly coupled to the third pulley 38. The magnets 54 and 56 are mounted on the inward facing side of the third pulley 38 in their same opposed relationship. A circular flange 130 is formed on the extremity of the housing 46 to mount the two switches 74 and 76, again in the same right angle relationship. In FIGS. 6 and 7, a pair of endless belts 34 are used, with each belt being positioned over only one pulley 26. In FIG. 8 a single belt 34 is used. Instead of the ball and chain arrangement of the previously described embodiments, a pair of rotatably mounted, frictional wheels 132 and 134 are provided adjacent opposed sides of the third pulley 38. These wheels 132 and 134 rotate with the belt 34 so as to tightly secure the belt 34 to the peripheral groove 42. In this embodiment the second peripheral groove 52 of the previous embodiments is eliminated. Moreover, the grooves 42 and 36 have an annular cross-sectional configuration, eliminating the need for the pockets 124 and the channels 126 of the previous embodiments. However, it should be understood that the ball and chain arrangement could also be used in this embodiment, therefore eliminating the need for the wheels 132 and 134.

In operation, the embodiment of FIGS. 6 through 8 operates in the same manner and with the same electrical circuitry as described in the previous embodiments. However, its advantages lies in the elimination of additional belts and a more direct and reliable coupling between the electric motor 44 and the third pulley 38. Moreover, a larger area is provided for the electric motor, in that the housing 46 extends into the tubular member 12.

Although particular embodiments of the invention have been shown and described here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A water sampler device for collecting a sample of water at a desired depth in a body of water, said water sampler device having an elongated tubular member, valve seat means mounted at each end of said tubular member; substantially spherical valve means mounted on each of said valve means in an initially closed position to prevent contaminated surface waters of said body of water from entering into said tubular member, valve rotating means connected to each of said valve means for consecutively rotating each of said valve means from said closed position to an open position to permit the flow of fluid through said tubular member when said device has arrived at said depth in said body of water and then to a further closed position to contain water in said tubular member, each said valve rotating means including valve pulley means rotatably mounted on the exterior of said tubular member, the improved said valve rotating means comprising:
   at least one endless belt mounted over at least one of the two said pulley means;
   an electric motor for moving said endless belt;
   first position changing means for energizing said electric motor to move said valve means from said initially closed position to said open position;
   second position changing means for energizing said electric motor to move said valve means from said open position to said further closed position.

2. The water sampler device according to claim 1, a third pulley means rotatably mounted between said two valve pulley means on the exterior of said tubular member so as to drivingly engage said endless belt;
   said electric motor means being coupled to said third pulley means for rotating said third pulley means.

3. The water sampler device according to claim 2, said first position changing means including first activating means electrically coupled to said electric motor for activating and energizing said electric motor to rotate said third pulley means and further including first deactivating means being disposed in position-sensing relationship to said third pulley means for deactivating said electric motor when said third pulley means has rotated through a first predetermined arc;
   said second position changing means including second activating means electrically coupled to said electric motor for activating and energizing said electric motor to rotate said third pulley means and further including second deactivating means being disposed in position-sensing relationship to said third pulley means for deactivating said electric motor when said third pulley means has rotated through a second predetermined arc.

4. The water sampler device according to claim 3, said first and second predetermined arcs being substantially 90 degrees.

5. The water sampler device according to claim 4, said first deactivating means including a first switch means operative to deactivate said electric motor;
   said second deactivating means including a second switch means operative to deactivate said electric motor.

6. The water sampler device according to claim 5, said first and second switch means being constructed to be magnetically enabled to deactivate said electric motor;
   said first and second deactivating means each including a magnet disposed on said pulley means, each said magnet being arranged and positioned to enable one of said switch means.

7. The water sampler device according to claim 6, said electrical motor having a drive shaft, said drive shaft being attached to said third pulley to rotatably mount said third pulley.

8. The water sampler device according to claim 7, said electric motor being mounted in a watertight housing, said housing being mounted in the wall of said tubular member with a substantial portion of said housing extending into the interior of said tubular member.

9. The water sampler device according to claim 8, said housing having a flange on its outer extremity which surrounds said drive shaft, said flange being positioned in parallel, adjacent, spaced relationship to said third pulley, said first and second switch means being disposed substantially at right angles to each other with respect to said drive shaft on said flange;
   said magnets being mounted in opposed relationship on the side of said third pulley which faces said flange to enable said switches.

10. The water sampler device according to claim 1 or 2,
   said first position changing means including first activating means electrically coupled to said electric motor for activating and energizing said electric motor to rotate one of said pulley means and further including first deactivating means being disposed in position-sensing relationship to said driven pulley means for deactivating said electric motor when said driven pulley means has rotated through a first predetermined arc;
   said second position changing means including second activating means electrically coupled to said electric motor for activating and energizing said electric motor to rotate said driven pulley means and further including second deactivating means being disposed in position-sensing relationship to said driven pulley means for deactivating said electric motor when said driven pulley means has rotated through a second predetermined arc.

11. The water sampler device according to claim 10, said first deactivating means including a first switch means operative to deactivate said electric motor;
   said second deactivating means including a second switch means operative to deactivate said electric motor.

12. The water sampler device according to claim 11, a pair of oppositely positioned magnets disposed on the periphery of said third pulley means;
   said first and second switch means being disposed substantially at right angles to each other with respect to the center of said third pulley means and adjacent to the periphery of said third pulley means.

13. The water sampler device according to claim 10 wherein said endless belt is mounted in looped relationship over both of said pulley means.

14. The water sampler device according to claim 8 or 9 wherein there are two said endless belts, one said endless belt being mounted in looped relationship over one of said valve pulley means and said third pulley means and the other said endless belt being mounted in looped relationship over the other said valve pulley means and said third pulley means, said third pulley means having a pair of circular grooves for receiving said endless belts.

* * * * *